US012558797B2

(12) United States Patent
Yu et al.

(10) Patent No.: US 12,558,797 B2
(45) Date of Patent: Feb. 24, 2026

(54) TRANSPARENT AND FLEXIBLE ELECTRONIC SKIN AND METHOD FOR FABRICATING THE SAME

(71) Applicant: City University of Hong Kong, Hong Kong (HK)

(72) Inventors: Xinge Yu, Hong Kong (HK); Jingkun Zhou, Hong Kong (HK); Jian Li, Hong Kong (HK); Huiling Jia, Hong Kong (HK)

(73) Assignee: City University of Hong Kong, Hong Kong (HK)

( * ) Notice: Subject to any disclaimer, the term of this patent is extended or adjusted under 35 U.S.C. 154(b) by 245 days.

(21) Appl. No.: 18/492,808

(22) Filed: Oct. 24, 2023

(65) Prior Publication Data

US 2025/0128426 A1 Apr. 24, 2025

(51) Int. Cl.
B25J 13/08 (2006.01)
B25J 13/00 (2006.01)
(Continued)

(52) U.S. Cl.
CPC ........... B25J 13/088 (2013.01); B25J 13/006 (2013.01); B25J 13/081 (2013.01); B25J 13/087 (2013.01); B25J 19/005 (2013.01); A61L 27/60 (2013.01)

(58) Field of Classification Search
CPC ...... B25J 13/088; B25J 13/006; B25J 13/081; B25J 13/087; B25J 19/005; A61L 27/60;
(Continued)

(56) References Cited

U.S. PATENT DOCUMENTS 9,927,933 B2 3/2018 Heim et al.
2010/0292945 A1* 11/2010 Reynolds ........... H03K 17/9622
702/65
(Continued)

OTHER PUBLICATIONS

Shanshan Zhu et al., "An artificial remote tactile device with 3D depth-of-field sensation," Sci. Adv. vol. 8 (eabo5314), p. 1-10.
(Continued)

*Primary Examiner* — Sahlu Okebato
(74) *Attorney, Agent, or Firm* — Idea Intellectual Limited; Sam T. Yip

(57) ABSTRACT

The present invention provides a transparent and flexible electronic skin with three-dimensional sensing capability. The electronic skin comprises: a substrate; an transparent and flexible electric field sensor disposed on the substrate; a control circuit disposed on the substrate; and a transparent and flexible protective layer encapsulating the electric field sensor and the control circuit. The electric field sensor includes a transmitter electrode; one or more receiver electrodes; and dielectric layer arranged between the transmitter electrode and receiver electrodes. The control circuit is connected to the electric field sensor and configured to: drive the transmitter electrode to transmit a reference signal to establish a quasi-static electrical near field; and process one or more measurement signals received by the one or more receiver electrodes respectively, each measurement signal is indicative of a distortion of the quasi-static electrical near field due to proximity of an object.

14 Claims, 14 Drawing Sheets

100

(51) Int. Cl.
B25J 19/00 (2006.01)
A61L 27/60 (2006.01)
(58) Field of Classification Search
CPC ..... G01R 29/12; A61B 5/1118; A61B 5/1121;
A61B 5/1125; A61B 5/1126; A61B
5/6801; A61B 2562/12; A61B 2562/164
See application file for complete search history.

(56) References Cited

U.S. PATENT DOCUMENTS

| | | | | |
|---|---|---|---|---|
| 2013/0123587 A1* | 5/2013 | Sarrafzadeh | ......... | A61B 5/7285 |
| | | | | 600/306 |
| 2015/0190079 A1* | 7/2015 | Yamaji | ............... | A61B 5/14552 |
| | | | | 29/841 |
| 2023/0158686 A1* | 5/2023 | Gao | ........................ | B25J 9/1694 |
| | | | | 700/246 |

OTHER PUBLICATIONS

Wenbo Liu et al., "Touchless interactive teaching of soft robots through flexible bimodal sensory interfaces," Nature Communications, 2022, vol. 13 (5030), p. 1-14.
M. E. Nelson et al., "Sensory acquisition in active sensing systems," Journal of Comparative Physiology A, 2006, vol. 192, p. 573-586.
H. W. Lissmann, "Continuous electrical signals from the Tail of a Fish, Gymnarchus niloticus Cuv.," Nature, 1951, vol. 167, p. 201-202.
C. C. Bell et al., "Mormyromast Electroreceptor Organs and Their Afferent Fibers in Mormyrid Fish: I. Morphology," The Journal of Comparative Neurology, 1989, vol. 286, p. 391-407.
Claude Derbin et al., "Ultrastructure of an Electroreceptor (Knollenorgan) in the Mormyrid Fish Gnathonemus petersii. I," J. Ultrastructure Research, 1968, vol. 22, p. 469-484.
M. V. L. Bennett, "Electroreceptors in Mormyrids," Cold Spring Harbor Symposia on Quantitative Biology, 1965, vol. 30, p. 245-262.
Joshua Reynolds Smith, "Electric Field Imaging," Massachusetts Institute of Technology, 1999, p. 1-216.
Martin Gottwald et al., "Electric-Color Sensing in Weakly Electric Fish Suggests Color Perception as a Sensory Concept beyond Vision," Current Biology, 2018, 28, p. 1-6.e1-e2.
Sarah Emily Skeels et al., "Sensory-motor integration in Gnathonemus petersii," University of Oxford, 2022.
Chunya Wang et al., "On-skin paintable biogel for long-term high-fidelity electroencephalogram recording," Sci. Adv., 2022, vol. 8 (eabo1396), p. 1-11.
Feargal Cleary, "Capacitive Touch Sensor Design Guide," Microchip, 2020, AN2934, p. 1-48.
Zainab Raheem, "Polymer Data Handbook," ResearchGate, 2019.
Bin Zhou et al., "Study on Measurement Error of Power Frequency Electric Field Intensity Caused by Change of Air Dielectric Constant with Humidity," IOP Conf. Ser.: Earth Environ. Sci., 2021, 772 (012022), p. 1-8.
Zach Jorgensen et al., "On Mouse Dynamics as a Behavioral Biometric for Authentication," ASIACCS '11, 2011, p. 476-482.
Qinghua Luo et al., "An Improved Trilateration Positioning Algorithm with Anchor Node Combination and K-Means Clustering," Sensors, 2022, vol. 22 (6085), p. 1-22.
Linlin Wang et al., "Applications and Prospects of Agricultural Unmanned Aerial Vehicle Obstacle Avoidance Technology in China," Sensors, 2019, vol. 19 (642), p. 1-16.
Nicole Malczan, "How Much Weight Can a Drone Carry? (lb & kg)," Droneblog, 2021.
"Product Specification of Forte Data Glove," BeBop Sensors, 2019, p. 1-3.
"Full specification of Manus XSENS metagloves," https://assets.website-files.com/61de97d15a7bb6441d9565c0/

639858e0613a273cb37e973f_Datasheet%20-%20Xsens%20Metagloves%20by%20MANUS.pdf, 2023.
Xin'an Huang et al., "Tracing the Motion of Finger Joints for Gesture Recognition via Sewing RGO-Coated Fibers Onto a Textile Glove," IEEE Sensors Journal, 2019, vol. 19, No. 20, p. 9504-9511.
Yiming Liu et al., "Electronic skin as wireless human-machine interfaces for robotic VR," Science Advances, 2022, vol. 8 (eabl6700), p. 1-11.
Ali Moin et al., "A wearable biosensing system with in-sensor adaptive machine learning for hand gesture recognition," Nature Electronics, 2021, vol. 4, p. 54-63.
"Full specification of Meta Quest 2," https://www.meta.com/tw/quest/products/quest-2/tech-specs/#tech-specs, 2024.
Arnon Amir et al., "A Low Power, Fully Event-Based Gesture Recognition System," IEEE Conference on Computer Vision and Pattern Recognition, 2017, p. 7243-7252.
"Full specification of ultraleap Leap Motion Controller," https://www.ultraleap.com/datasheets/Leap_Motion_Controller_Datasheet_April_2020.pdf, 2020.
Yong Wang et al., "Multi-Hand Gesture Recognition Using Automotive FMCW Radar Sensor," Remote Sensing, 2022, 14 (2374), p. 1-17.
Shahzad Ahmed et al., "Hand Gestures Recognition Using Radar Sensors for Human-Computer-Interaction: A Review," Remote Sensing, 2021, 13 (527), p. 1-24.
"Video of Google Project Soli," https://www.youtube.com/watch?v=0QNiZfSsPc0&ab_channel=GoogleATAP, Google ATAP, 2015.
Jaime Lien et al., "Soli: Ubiquitous Gesture Sensing with Millimeter Wave Radar," ACM Trans. Graph., 2016, vol. 35, No. 4, Article 142, p. 1-19.
"Full specification of TDK SamrtSonic," https://invensense.tdk.com/smartsonic/, 2024.
"Ultra-low Power Integrated Ultrasonic Time-of-Flight Range Sensor," TDK, 2020, p. 1-20.
Zi Hao Guo et al., "Bioinspired soft electroreceptors for artificial precontact somatosensation," Sci. Adv., 2022, vol. 8 (eabo5201), p. 1-9.
"Gesture Recognition Market Size, Share & Trends Analysis Report By Technology (Touch-based, Touchless), By Industry (Automotive, Consumer Electronics, Healthcare), By Region, And Segment Forecasts, 2023-2030," Grand View Research, https://www.grandviewresearch.com/industry-analysis/gesture-recognition-market, 2024, GVR-2-68038-019-4.
"Gesture Recognition Market Size & Share Analysis—Growth Trends & Forecasts (2024-2029)," Mordor Intelligence, https://www.mordorintelligence.com/industry-reports/gesture-recognition-market, 2024.
"Gesture Recognition Market Size, Share & Trends Analysis Report By Technology (Touch-based, Touchless), By Industry (Automotive, Consumer Electronics, Healthcare), And Segment Forecasts, 2019-2025," Research and Markets, https://www.researchandmarkets.com/reports/4751763/gesture-recognition-market-size-share-and-trends, 2019.
"Gesture Recognition Market Size to Hit $51.48 Billion, Globally, by 2028 with 22.3% CAGR—Growth Report by The Insight Partners," The Insight Partners, 2023.
"Global Gesture Recognition Market By Type (Touchless—CapacitiveElectric Field, Infrared Array, Ultrasonic Technology, 2D Camera-Based Technology; Touch Based—Multi-Touch System, Motion Gesture) , vertical (Consumer Electronics, Automotive, Healthcare) By Region, Industry Analysis and Forecast, 2017-2023," KBV reseaarch, https://www.kbvresearch.com/gesture-recognition-market/, 2017.
"Global Robot Sensor Market Size To Surpass $5.5 Billion By 2030 | CAGR 11.6%," Spherical Insights LLP, 2023.
"Robotic Sensors Market Size, Share, Competitive Landscape and Trend Analysis Report by Type, by Vertical : Global Opportunity Analysis and Industry Forecast, 2021-2031," Sensors And Controls, https://www.alliedmarketresearch.com/robotic-sensors-market-A16956, 2022.
"Robotic Sensors Market Size & Share Analysis—Growth Trends & Forecasts (2024-2029)," Mordor Intelligence, https://www.mordorintelligence.com/industry-reports/robotic-sensors-market, 2024.

(56) References Cited

OTHER PUBLICATIONS

"Robot Sensor Market Size—By Product (Force/Torque, Vision, Ultrasonic, Tactile, Laser Range, Proximity), Robot Type (Industrial, Service, Collaborative), Application (Manufacturing, Logistics, Defense, Agriculture, Medical, Domestic, Entertainment) & Forecast, 2022-2028," Global Market Insights, https://www.gminsights.com/industry-analysis/robot-sensor-market, 2022, GMI2802.

Rossella Gratton et al., "Unraveling the Role of Sex Hormones on Keratinocyte Functions in Human Inflammatory Skin Diseases," Int. J. Mol. Sci., 2022, 23 (3132), p. 1-19.

Hai Le Thanh Nguyen et al., "Role of Antimicrobial Peptides in Skin Barrier Repair in Individuals with Atopic Dermatitis," Int. J. Mol. Sci., 2020, 21 (7607), p. 1-17.

Ehrhardt Proksch et al., "The skin: an indispensable barrier," Experimental Dermatology, 2008, vol. 17, p. 1063-1072.

Stephanie J. Benight et al., "Stretchable and Self-Healing Polymers and Devices for Electronic Skin," Progress in Polymer Science, 2013, vol. 38, p. 1961-1977.

Xinge Yu et al., "Skin-integrated wireless haptic interfaces for virtual and augmented reality," Nature, 2019, vol. 575, p. 473-479.

Dengfeng Li et al., "Recent progress of skin-integrated electronics for intelligent sensing," Light: Advanced Manufacturing, 2021, vol. 2 (4), p. 1-20.

Chunki Yiu et al., "Soft, stretchable, wireless intelligent three-lead electrocardiograph monitors with feedback functions for warning of potential heart attack," SmartMat, 2022, p. 1-17.

Ha Uk Chung et al., "Binodal, wireless epidermal electronic systems with in-sensor analytics for neonatal intensive care," Science, 2019, vol. 363 (eaau0780).

Xingcan Huang et al., "Epidermal self-powered sweat sensors for glucose and lactate monitoring," Bio-Design and Manufacturing, 2022, vol. 5, p. 201-209.

Mallika Bariya et al., "Wearable sweat sensors," Nature Electronics, 2018, vol. 1, p. 160-171.

Kunhyuck Lee et al., "Mechano-acoustic sensing of physiological processes and body motions via a soft wireless device placed at the suprasternal notch," Nature Biomedical Engineering, 2020, vol. 4, p. 148-158.

Dengfeng Li et al., "Touch IoT enabled by wireless self-sensing and haptic-reproducing electronic skin," Sci. Adv., 2022, vol. 8 (eade2450), p. 1-13.

Kuanming Yao et al., "Encoding of tactile information in hand via skin-integrated wireless haptic interface," Nature Machine Intelligence, 2022, vol. 4, p. 893-903.

Kyun Kyu Kim et al., "A substrate-less nanomesh receptor with meta-learning for rapid hand task recognition," Nature Electronics, 2023, vol. 6, p. 64-75.

Kyun Kyu Kim et al., "Transparent wearable three-dimensional touch by self-generated multiscale structure," Nature Communications, 2019, 10 (2582), p. 1-8.

Chong-Chan Kim et al., "Highly stretchable, transparent ionic touch panel," Science, 2016, vol. 353 (6300), p. 682-687.

Hyunseok Shim et al., "Stretchable elastic synaptic transistors for neurologically integrated soft engineering systems," Sci. Adv., 2019, vol. 5 (eaax4961), p. 1-11.

Sushmita Mitra et al., "Gesture Recognition: A Survey," IEEE Transactions on Systems, Man, and Cybernetics—Part C: Applications and Reviews, 2007, vol. 37, No. 3, p. 311-324.

Jakub Galka et al., "Inertial motion sensing glove for sign language gesture acquisition and recognition," IEEE Sensors Journal, 2016, vol. 16 (16), p. 6310-6316.

Bin Fang et al., "3D human gesture capturing and recognition by the IMMU-based data glove," Neurocomputing, 2018, vol. 277, p. 198-207.

Hanxiang Wu et al., "Fabric-based self-powered noncontact smart gloves for gesture recognition," J. Mater. Chem. A., 2018, vol. 6, p. 20277-20288.

Feng Wen et al., "Machine Learning Glove Using Self-Powered Conductive Superhydrophobic Triboelectric Textile for Gesture Recognition in VR/AR Applications," Adv. Sci., 2020, vol. 7, 2000261, p. 1-15.

Jipeng Yan et al., "A Lightweight Ultrasound Probe for Wearable Human-machine Interfaces," IEEE Sensors Journal, 2019, vol. 19, p. 5895-5903.

Young-Tae Kwon et al., "All-printed nanomembrane wireless bioelectronics using a biocompatible solderable graphene for multimodal human-machine interfaces," Nature Communications, 2020, vol. 11 (3450), p. 1-11.

Takeshi Kamijo et al., "A touchless user interface based on a near-infrared-sensitive transparent optical imager," Nature Electronics, 2023, vol. 6, p. 451-461.

Gelbert Santiago Cañón Bermúdez et al., "Magnetosensitive e-skins with directional perception for augmented reality," Sci. Adv., 2018, vol. 4 (eaao2623), p. 1-9.

* cited by examiner

100

101

102

100 (101)

140

121

123

122

110

120

100 (102)

140

130

110

150

120

122

605

602

603

604

601

RX

121

TX

Interactive space

Electronic skin

TRANSPARENT AND FLEXIBLE ELECTRONIC SKIN AND METHOD FOR FABRICATING THE SAME

COPYRIGHT NOTICE

FIELD OF THE INVENTION

The present invention generally relates to electronic skin technology. More specifically the present invention relates to a transparent and flexible electronic skin with three-dimensional sensing capability.

BACKGROUND OF THE INVENTION

Three-dimensional sensing capability is crucial for human-machine interaction and machine perception in the three-dimensional world. With the popularity of topics such as metaverses and teleoperated robots in recent years, 3D spatial perception functions have become more and more indispensable. However, conventional skin electronics are limited to acquiring only two-dimensional spatial data through physical contact.

The field of 3D gesture recognition has seen rapid advancements in recent years. Some state-of-art wearable devices can detect finger movements in space, relying on inertial sensors, strain/stress sensors, ultrasound, or electrocardiogram signals. These devices often have limitations in recognizing a diverse range of gestures and dynamically tracking finger movements in space. Other strategies based on image analysis, magnetic fields, radar technology, or electrostatic principles come with their own challenges, such as complex processing algorithms, bulky device sizes, high power consumption, sensitivity to change in working environments and so on.

SUMMARY OF THE INVENTION

One objective of the present invention is to provide a transparent and flexible electronic skin with three-dimensional sensing capability, simpler processing algorithm, compact size, low power consumption and adaptive to various working environments. Another objective of the present invention is to provide a method fabricating a transparent and flexible electronic skin which is suitable for mass production.

According to one aspect of the invention, a transparent and flexible electronic skin, which is inspired by active sensing system of Mormyroidea, is provided. The transparent and flexible electronic skin comprises: a transparent and flexible substrate; a transparent and flexible electric field sensor disposed on the substrate. The electric field sensor comprises: a transparent and flexible transmitter electrode; and one or more transparent and flexible receiver electrodes. The electronic skin further comprises a control circuit disposed on the substrate and connected to the electric field sensor and a transparent and flexible protective layer encapsulating the electric field sensor and the control circuit. The control module is configured to: drive the transmitter electrode to transmit a reference signal to establish a quasi-static electrical near field around the electric field sensor; and process one or more measurement signals received by the one or more receiver electrodes respectively, each measurement signal is indicative of a distortion of the quasi-static electrical near field due to proximity of an object to a corresponding receiver electrode.

According to another aspect of the invention, a method for fabricating a transparent and flexible electronic skin is provided. The method comprises: moulding a transparent and flexible material to form a patterned transparent and flexible substrate; dispensing a first conductive transparent gel on the patterned transparent and flexible substrate to form a transmitter electrode; forming a control circuit on the patterned transparent and flexible substrate; moulding the transparent and flexible material to form a patterned transparent and flexible dielectric layer; dispensing a second conductive transparent gel on the patterned transparent and flexible dielectric layer to form one or more receiver electrodes; attaching the dielectric layer on the substrate such that the transmitter electrode is spaced apart from the one or more receiver electrodes through the dielectric layer to form an electric filed sensor; and encapsulating the control circuit and the electric field sensor with the transparent and flexible material.

By employing bio-gel as electrode material and silicone polymers as substrates/dielectric layers, the electronic skin provided by the present invention has exceptional stretchability and light transmittance. This unique feature enables seamless integration with existing surfaces, such as screens, without imposing a significant reduction in brightness. Furthermore, the electric filed sensor in the provided electronic skin exhibit excellent performance in 3D sensing even when being submerged underwater. Through practical evaluation involving PCs, robots, and drones, the immense application potential of the present invention has been showcased in human-machine interaction (such as touch screens), virtual-reality space (such as metaverse) and robotics application (such as remote robot control) scenarios demanding three-dimensional manipulation and perception. Moreover, the feasibility of mass production through printing technology substantially reduces manufacturing costs.

The utilization of a bio-gel as an electrode not matches the performance of traditional metal electrodes but also enhances the device's stretchability, eliminating concerns about metal fatigue. The provided electronic skin is lightweight, transparent, wireless. Moreover, the overall performance of the electronic skin affixed to human skin can be significantly enhanced when using the human skin as a grounding system. Moreover, the provided electronic skin demonstrates superior underwater performance, indicating great potential for underwater applications.

BRIEF DESCRIPTION OF THE DRAWINGS

Aspects of the present disclosure may be readily understood from the following detailed description with reference to the accompanying figures. The illustrations may not necessarily be drawn to scale. That is, the dimensions of the various features may be arbitrarily increased or reduced for clarity of discussion. There may be distinctions between the artistic renditions in the present disclosure and the actual apparatus due to manufacturing processes and tolerances. Common reference numerals may be used throughout the drawings and the detailed description to indicate the same or similar components.

DETAILED DESCRIPTION

In the following description, details of the present invention are set forth as preferred embodiments. It will be apparent to those skilled in the art that modifications, including additions and/or substitutions may be made without departing from the scope and spirit of the invention. Specific details may be omitted so as not to obscure the invention; however, the disclosure is written to enable one skilled in the art to practice the teachings herein without undue experimentation.

In accordance with various aspects of the present invention, a transparent and flexible electronic skin with three-dimensional sensing capability, which is inspired by active sensing system of Mormyroidea, is provided. Mormyroidea, a superfamily of weakly electric fish, are capable of using electric fields to detect prey hidden in the sediment underwater. These fishes generate a weak electric field through electric organs located in their tail, and then sense distortions in the electric field caused by the target through electroreceptors that are present throughout their body.

Figure 1:
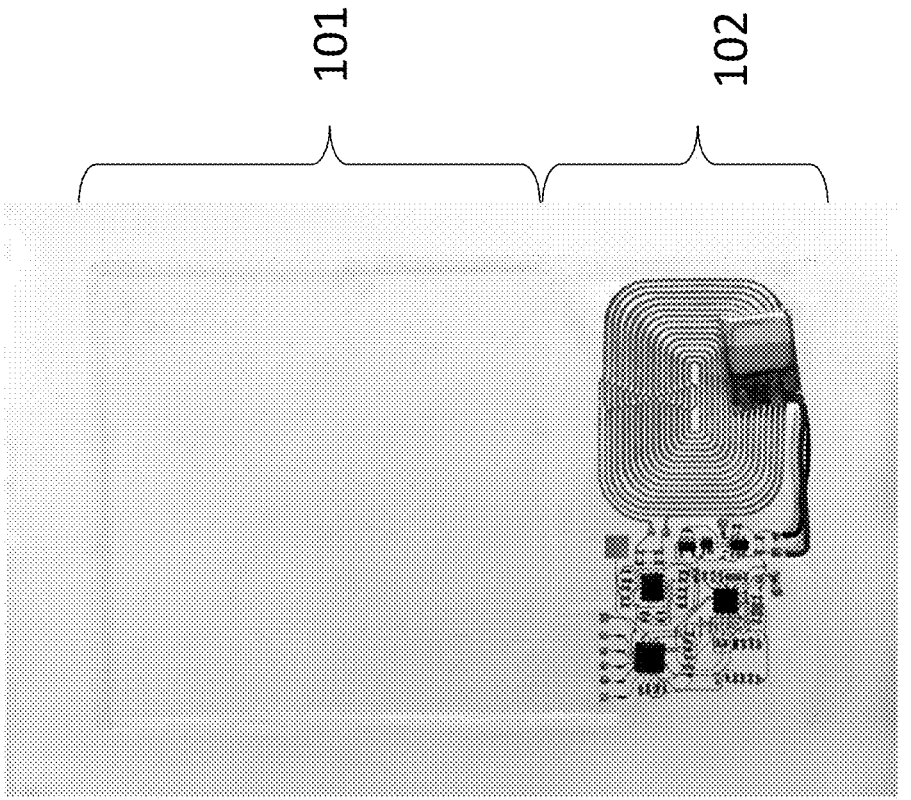
FIG. 1 illustrates a photo of a transparent and flexible electronic skin according to one embodiment of the present invention.
Figure 2A:
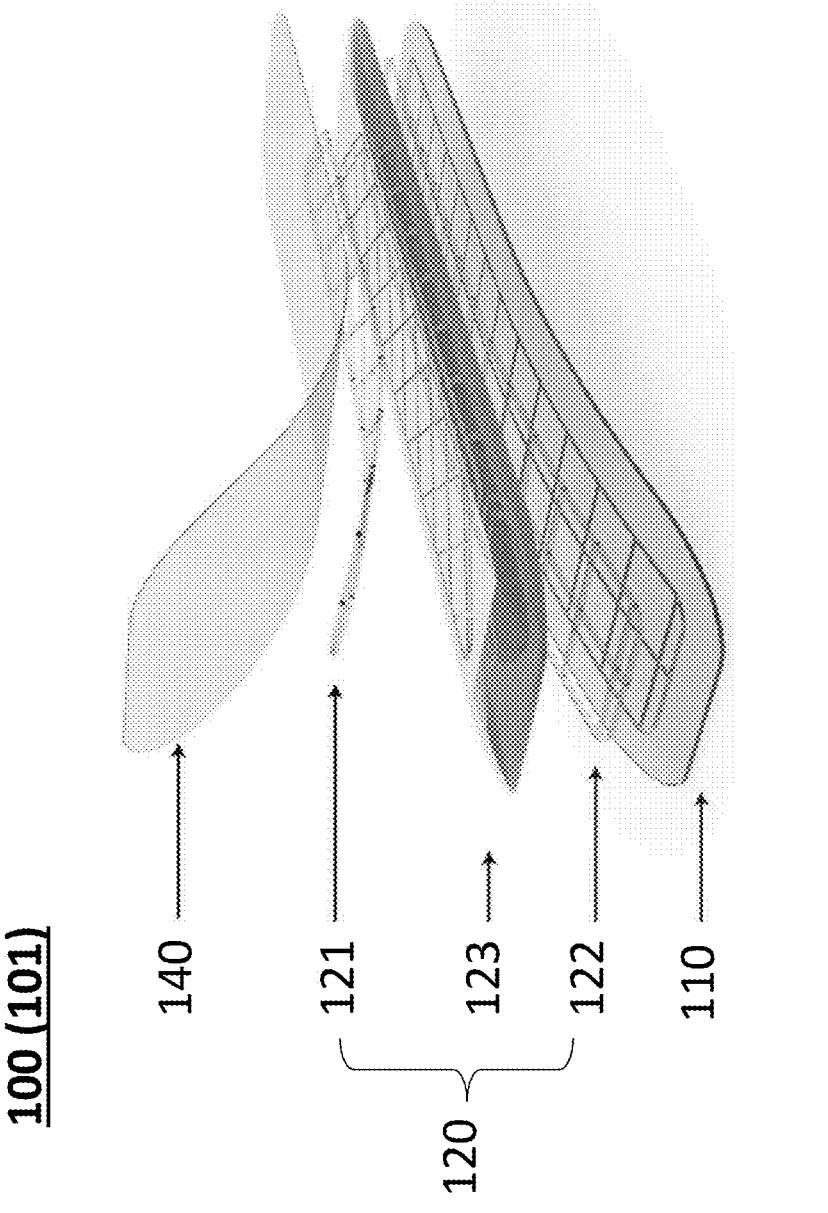
FIGS. 2A and 2B illustrate schematic exploded views of the sensing and circuitry parts of the electronic skin respectively.
Figure 2B:
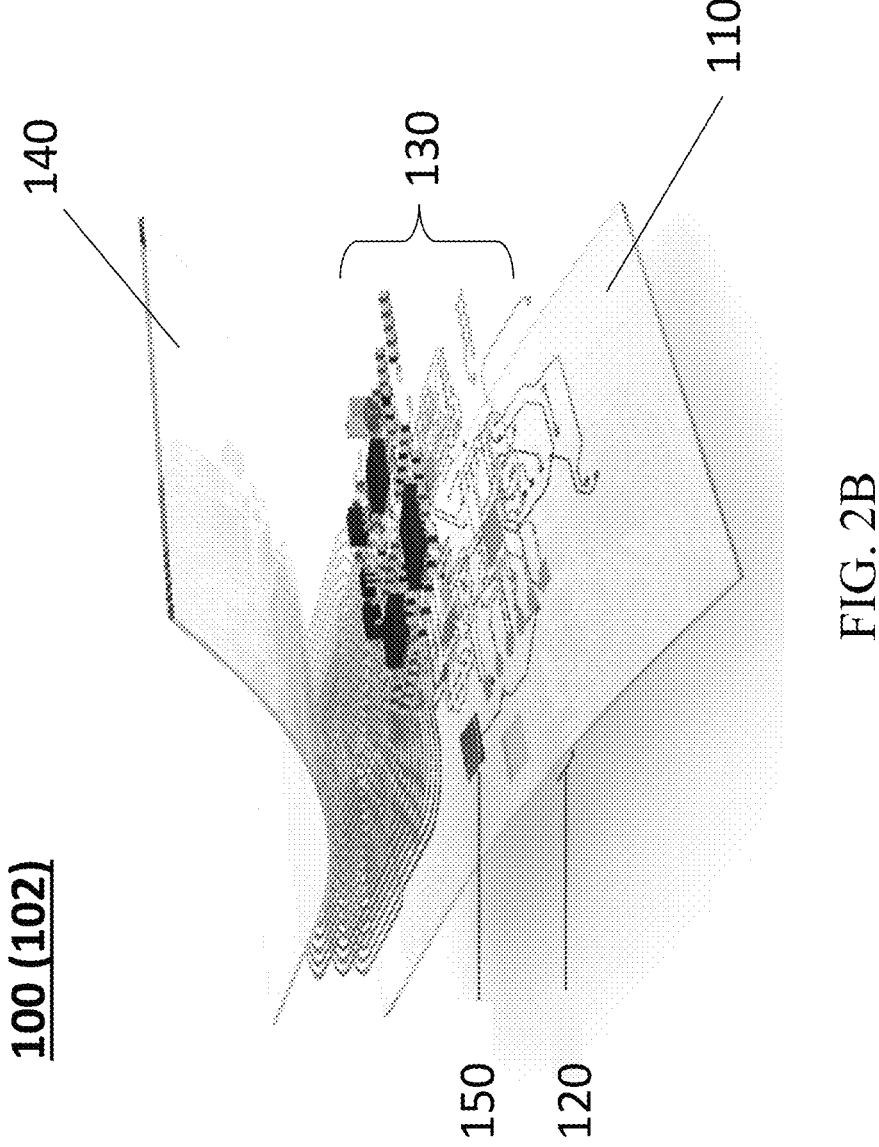

FIG. 1 illustrates a photo of a transparent and flexible electronic skin 100 according to one embodiment of the present invention. The electronic skin 100 may be divided into a sensing part 101 and a circuitry part 102. FIGS. 2A and 2B illustrate schematic exploded views of the sensing and circuitry parts respectively. As shown, the electronic skin 100 comprises a transparent and flexible substrate 110, a transparent and flexible electric filed sensor 120; a control circuit 130; and a transparent and flexible protective layer 140 for encapsulating the electric field sensor and the control circuit to protect the electric field sensor and the control circuit from external environmental factors, such as moisture or dust.

FIGS. 2A and 2B illustrate close-up views of the sensing parts 101 and circuitry part 102 of the electric field sensor 120 respectively. As shown, the electric field sensor 120 is disposed on the substrate 110 and covered by the protective layer 140. That is, the electric field sensor 120 is arranged between the substrate 110 and the protective layer 140. The electric field sensor 120 comprises a transparent and flexible transmitter electrode 121; one or more transparent and flexible receiver electrodes 122; and a transparent and flexible dielectric layer 123 arranged between the transmitter electrode and receiver electrodes.

Preferably, the substrate 110, dielectric layer 123 and protective layer 140 are made of silicone polymer, such as polydimethylsiloxane (PDMS). The electrodes may be made of conductive transparent gel, such as biogel containing NaCl and having an ionic conductivity of 34.3 S/m.

The control circuit 130 is disposed on the substrate 110 and connected to the electric field sensor 120. The control circuit 130 is configured to drive the transmitter electrode 121 to transmit a reference signal to establish a quasi-static electrical near field around the electric field sensor 120; and process one or more measurement signals received by the one or more receiver electrodes 122 respectively. Each measurement signal is indicative of a distortion of the quasi-static electrical near field (i.e., the reference signal) due to proximity of an object (e.g., a finger) to a corresponding receiver electrode.

Figure 3:
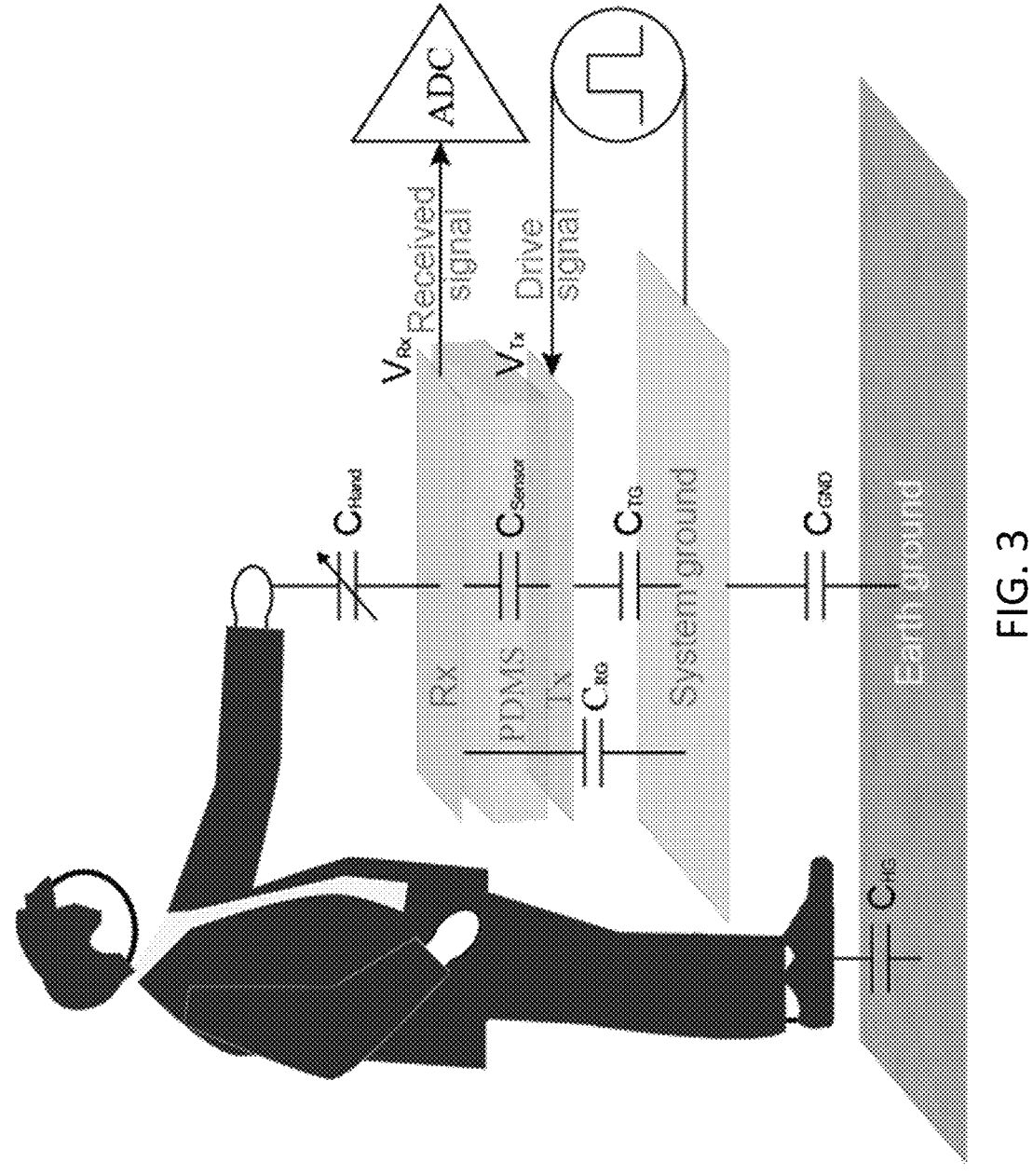
FIG. 3 shows an equivalent circuit model of the electric field sensor according to one embodiment of the present invention.

FIG. 3 shows an equivalent circuit model of the electric field sensor. The transmitter (Tx) and receiver (Rx) electrodes of the electric field sensor, along with the dielectric layer in the middle, form a flat capacitor with a capacitance value of $C_{Sensor}$. A variable capacitance is formed between the object (or target) to be detected or sensed (such as a human hand) and the receiver electrode, having a capacitance value denoted as $C_{Hand}$. Further, the capacitance formed by the two electrodes and the system ground are $C_{RG}$ and $C_{TG}$, respectively. When using an external power supply, the system ground and earth ground are assumed to be equivalent. The capacitance between the target to be sensed and the earth ground is $C_{HG}$. When using battery power, there is an additional capacitance between the system ground and earth ground, denoted as $C_{GND}$. For sake of simplicity, $C_{GND}$ and $C_{HG}$ is omitted from the model. Given the driving signal $V_{Tx}$ applied to the Tx electrode, the received signal $V_{Rx}$ received by the Rx electrode can be expressed as:

$$V_{Rx} = V_{Tx} \times \frac{C_{Sensor}}{C_{Sensor} + C_{RG} + C_{Hand}} \tag{1}$$

This received signal $V_{Rx}$ is dependent on the capacitance values $C_{Sensor}$ and $C_{Hand}$, which can be estimated using the flat capacitor formula $C = \varepsilon \cdot \varepsilon_0 \cdot S/d$, where $\varepsilon$ is the relative dielectric constant, $\varepsilon_0$ is the vacuum dielectric constant, S is the effective area and d is the distance.

Figure 4B:
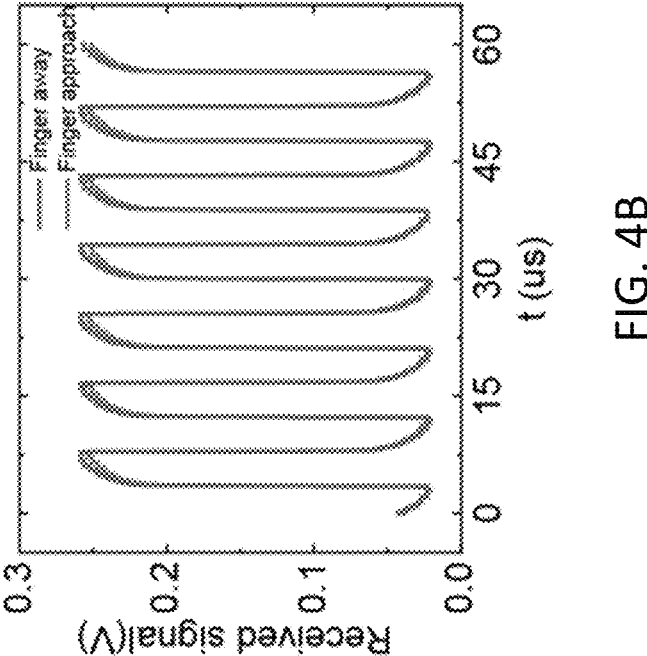
FIG. 4B shows voltage signal received by receiver electrode.
Figure 4A:
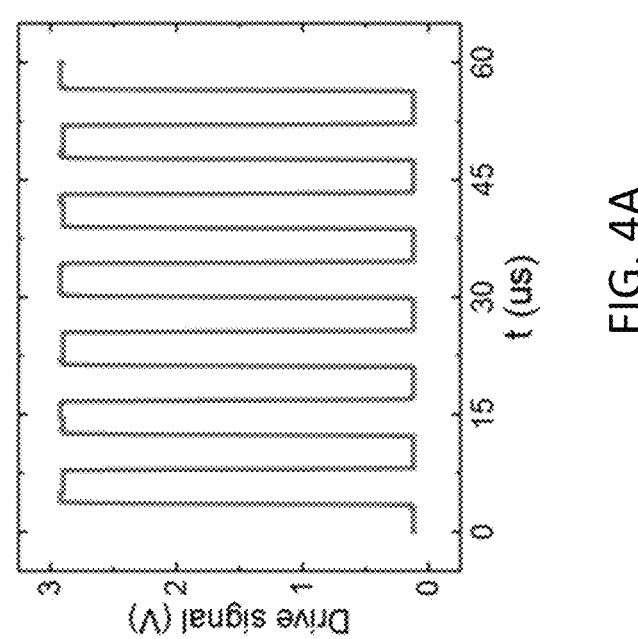
FIG. 4A shows a high frequency square wave voltage signal used by the control circuit to drive transmitter electrode.

In some embodiments, the transmitter electrode may be driven by the control circuit with a high frequency square wave signal with amplitude of around 3V (as shown in FIG. 4A). The frequency of the square wave signal can be in a range of 44 k to 115 kHz.

Figure 5:
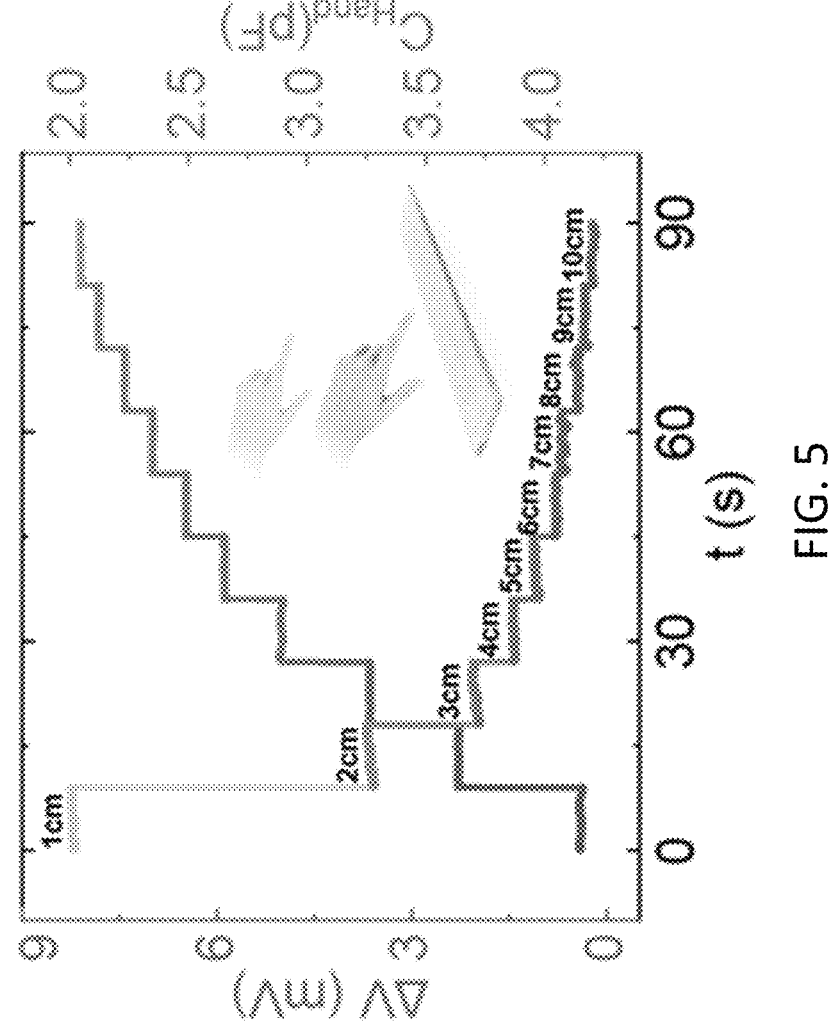
FIG. 5 shows a plot of capacitance and received voltage with distance obtained by placing a target at various distances from the electric field sensor in the electronic skin.

When the hand is approached to the sensor, $C_{Hand}$ increases (S increases and d decreases in the flat capacitor formula), which leads to decrease of received signal $V_{Rx}$ (as shown in FIG. 4B). The plot of capacitance and received voltage with distance (FIG. 5) can be obtained by placing the target at various distances from the sensor. According to Equation (1), when the variation range of $C_{Hand}$ is fixed, to obtain a larger response, that is, make the variation of $V_{Rx}$ as large as possible, the value of $C_{Sensor}$ should be close to $C_{RG}+C_{Hand}$, and $C_{RG}+C_{Hand}$ should be as small as possible.

The performance of the electronic skin may be affected by a variety of factors, such as the power source (USB or battery), the presence of a grounded shield beneath it, whether it is attached to the skin, and so on. When the device is powered by a battery, $C_{HG}$ and $C_{GND}$ cannot be ignored, resulting in a decrease in device performance. For example, when the electronic skin is directly attached to human skin, regardless of what types of power supply is used, its performance is significantly reduced due to the capacitance formed by the Rx electrode and the skin being added to the denominator of Equation (1) as a non-negligible term. To address this issue, the electronic skin 100 may further comprise a grounding pad 150 configured for electrically connecting a system ground of the electronic skin 100 to an earth ground.

Figure 6:
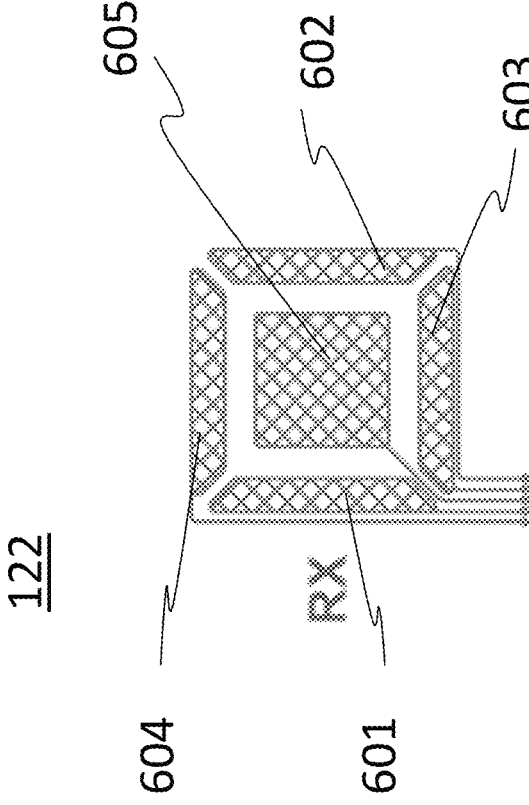
FIG. 6 shows an exemplary electrode design according to one embodiment of the present invention.
Figure 6:
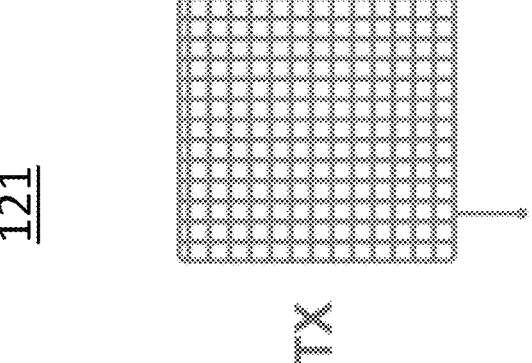

FIG. 6 illustrates an exemplary electrode design according to one embodiment of the present invention. As shown, each of the transmitter electrode and receiver electrodes may have a mesh pattern formed with conductive mesh lines. The receiver electrodes 122 may include four peripheral receiver electrodes 601 to 604 positioned at four peripheral regions of the electric filed sensor respectively; and a central receiver electrode 605 positioned at a central region of the electric field sensor.

Figure 7:
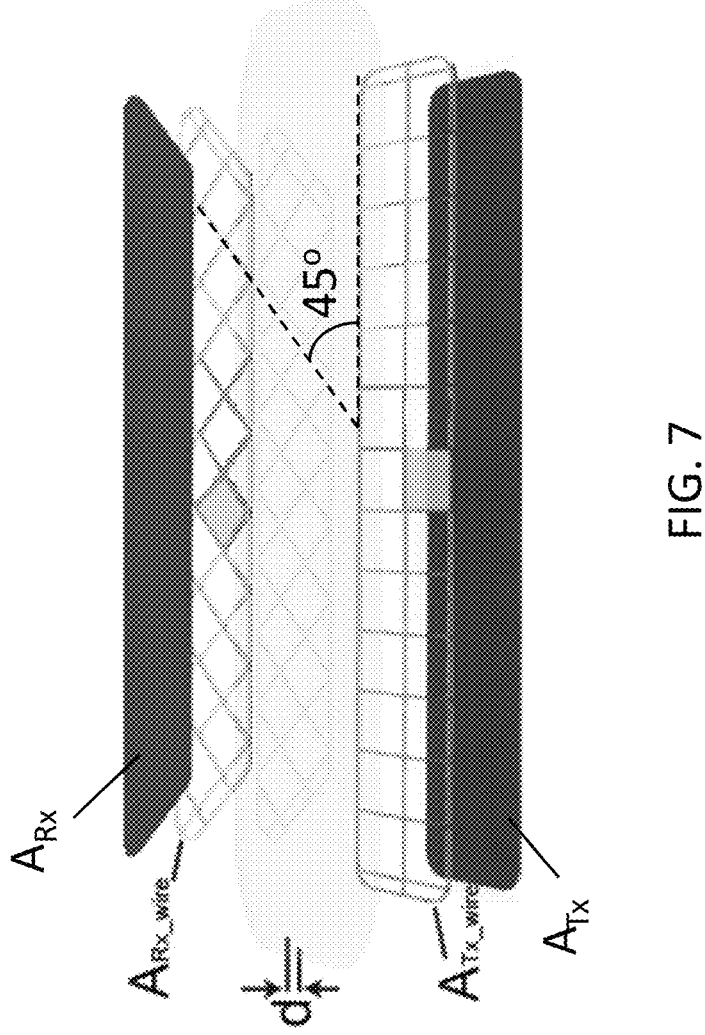
FIG. 7 shows some critical parameters of the electronic skin according to one embodiment of the present invention.

FIG. 7 shows some critical parameters of the electronic skin. Preferably, a ratio of the total conductive area of the transmitter electrode (denoted as $A_{Tx\_wire}$, i.e., total area of conductive mesh lines) to the total electrode area of the transmitter electrode (denoted as $A_{Tx}$) is equal or less than 8.1%. Preferably, a ratio of the total conductive area of the receiver electrode (denoted as $A_{Rx\_wire}$, i.e., total area of conductive mesh lines) to the total electrode area of the receiver electrode (denoted as $A_{Rx}$) is equal or less than 12.4%. The dielectric layer may have a thickness (denoted as d) in a range from 0.75 mm to 0.85 mm. Preferably, the thickness of the dielectric layer is equal to 0.8 mm.

Typically, the thickness of the substrate is 0.4 mm, the thickness of the dielectric layer is 0.6~ 0.8 mm, the thickness of the biogel trace is 0.2 mm, and the width is 0.2 mm. The overall thickness of the electronic skin is ~1 mm.

Moreover, an orientation of the conductive mesh lines of the transmitter electrode is substantially 45° different from an orientation of the conductive mesh lines of the receiver electrodes. In other words, the conductive mesh lines of the transmitter electrode are arranged to have an inclination angle substantially equal to 45° with respect to the conductive mesh lines of the receiver electrode.

Figure 8:
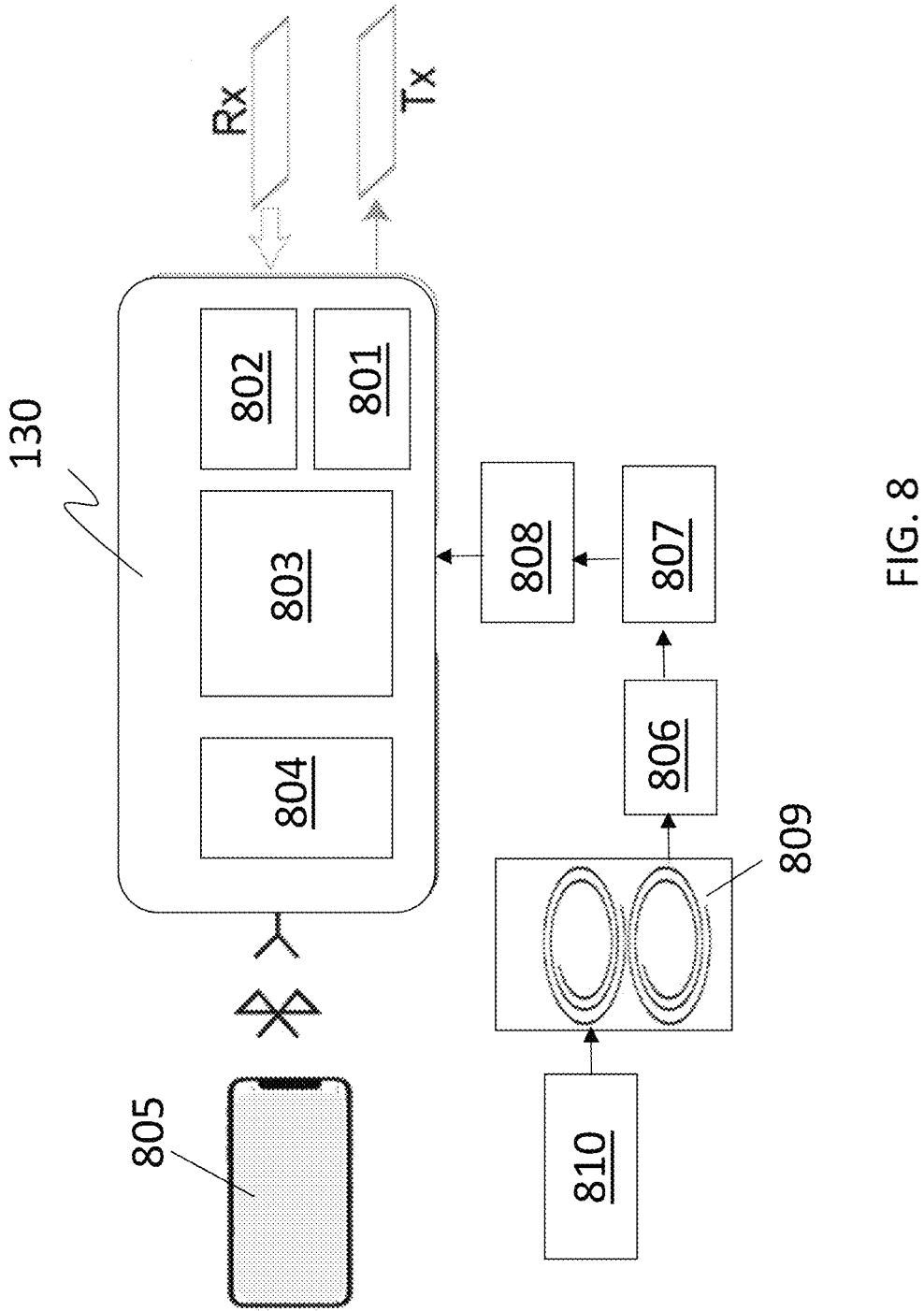
FIG. 8 illustrate a functional block diagram of the control circuit 130 according to one embodiment of the present invention.

FIG. 8 illustrate a functional block diagram of the control circuit 130 according to one embodiment of the present invention. The control circuit may include a signal driver 801 configured to drive the transmitter (Tx) electrode to transmit the reference signal; and an analogy-to-digital converter 802 configured to convert the one or more measurement signals received from the receiver (Rx) electrodes to one or more digital signals respectively. The control circuit may further include a microprocessor 803 configured to: process the one or more digital signals to calculate one or more distances of the object relative to the one or more receiver electrodes respectively; and analyze the one or more calculated distances to determine a position/gesture data of the object. The control circuit may further comprise a wireless communication unit 804 configured to send the position/gesture data to a remote device 805, such as a mobile phone. In some embodiments, the wireless communication unit 804 is a Bluetooth Low Energy (BLE) communication module.

In some embodiments, distance of the object relative to each of the one or more receiver electrode is calculated by the processor 803 based on a least squares multilateration algorithm.

Preferably, the electronic skin may further comprise a lithium-ion battery 806; a capacitive touch switch 807 for switching connection of the battery 806 to the control unit; and a low-dropout regulator (LDO) 808 for regulating a voltage of the battery to a fixed, direct-current voltage to the control circuit.

The electronic skin may further comprise a wireless charger receiver 809 configured to receive electromagnetic energy from a wireless charger transmitter 810 and convert the received electromagnetic energy into DC voltage to charge the lithium-ion battery 806.

Figure 9:
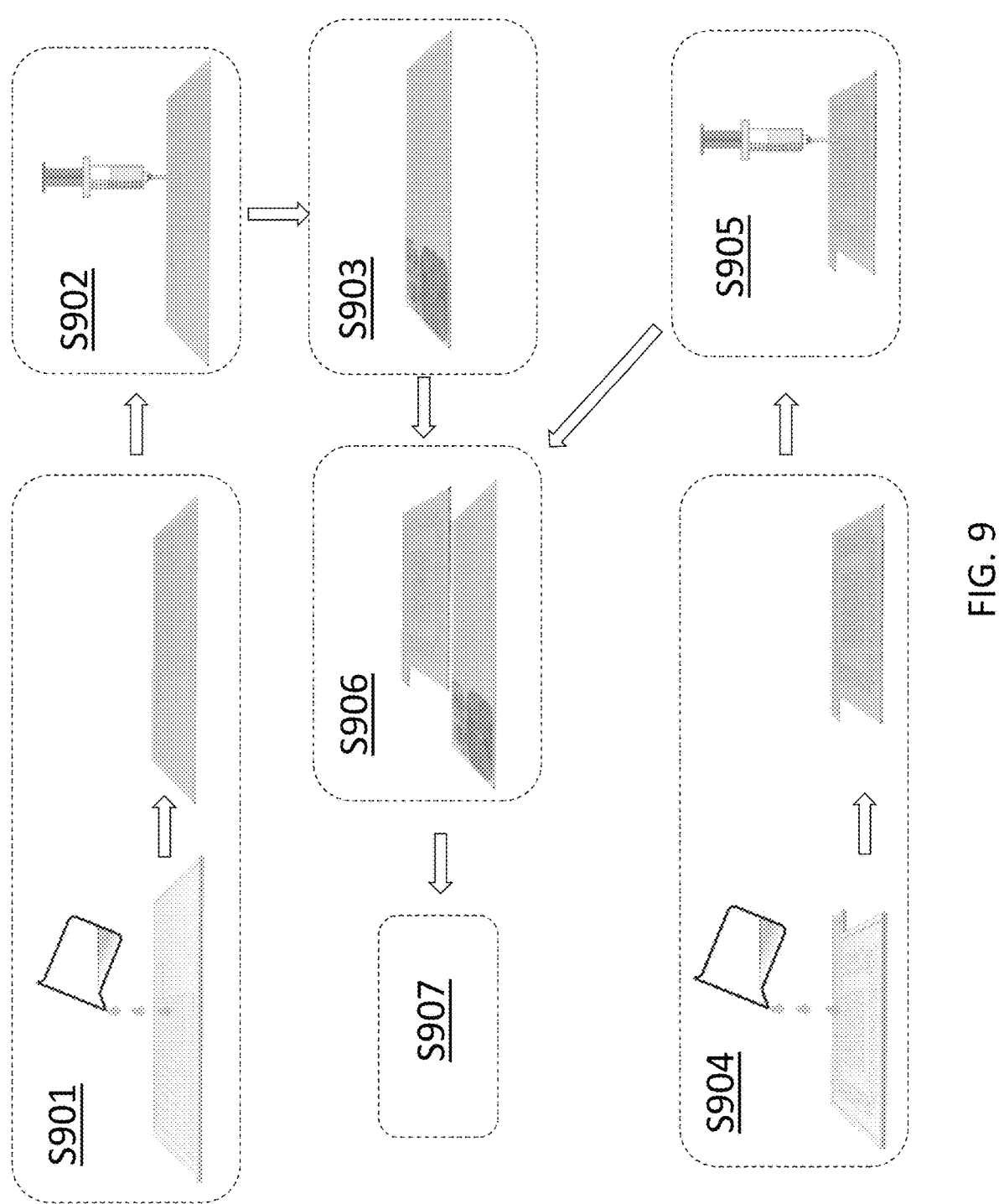
FIG. 9 shows a schematic flow of a method for fabricating a transparent and flexible electronic skin according to one embodiment of the present invention.

FIG. 9 shows a schematic flow of a method for fabricating a transparent and flexible electronic skin according to one embodiment of the present invention. As shown, the method includes:

S901: moulding a transparent and flexible material with a mold to form a patterned transparent and flexible substrate.

S902: dispensing a conductive transparent gel on the patterned transparent and flexible substrate to form a transmitter electrode;

S903: forming a control circuit on the patterned transparent and flexible substrate;

S904: moulding the transparent and flexible material with a mold to form a patterned transparent and flexible dielectric layer;

S905: dispensing the conductive transparent gel on the patterned transparent and flexible dielectric layer to form one or more receiver electrodes;

S906: attaching the dielectric layer on the substrate such that the transmitter electrode is spaced apart from the one or more receiver electrodes through the dielectric layer to form an electric filed sensor; and S907: encapsulating the control circuit and the electric field sensor with the transparent and flexible material.

In some embodiments, a light-curing 3D printer (Creality Halot Box, Shenzhen Creality 3D Technology Co., Ltd.) with resin (Polyacrylate) may be used to manufacture the molds with patterns for forming the patterned transparent and flexible substrate/dielectric layer.

In some embodiments, a silicone polymer, such as PDMS (Sylgard 184, Dow Corning Corporation, 20:1) may be used the transparent and flexible material. In step S901/S904, the PDMS is poured into the mold and cured at 100° C. for 30 minutes to obtain the patterned transparent and flexible substrate/dielectric layer. In step S907, the PDMS is used to encapsulate the control circuit and the electric field sensor and left to cure at room temperature overnight.

In some embodiments, the conductive transparent gel may be prepared by: dissolving sodium chloride, citric acid, sodium citrate and glycerol in deionized water to form a first solution; and dissolving gelatin powder (300-g Bloom) in the first solution to form the conductive transparent gel.

In one embodiment, the weight ratio of sodium chloride, citric acid, sodium citrate, glycerol and deionized water in the first solution is substantially equal to 10:1:10:60:80. The weight ratio of the first solution and the gelatin power is substantially equal to 4:1. For instance, the conductive transparent gel may be prepared by dissolve 1 g of sodium chloride, 0.1 g of citric acid, 1 g of sodium citrate and 6 g of glycerol in 8 ml of deionized water, mix on a stirrer for 20 minutes, after which 4 g of gelatin powder should be added and heated in an oven at 75° C. for 4 hours to fully dissolve the gelatin. After cooling, the liquid will transform into a gel due to the physical cross-linking of the gelatin chains and the chemical cross-linking of the citrate ions with the gelatin chains. When using the biogel, just heat it to revert it to liquid state, which will allow it to be extruded from the needle while dispensing, and as the temperature drops to room temperature, the gel will revert back to tis gel-like state and adhere to the substrate.

In steps S902/S905, the biogel is placed in a barrel. The biogel is then heated to 50° C. and injected/dispensed into the electrode pattern channels on the PDMS substrate/dielectric layer through a printing or dispensing process to form the transmitter/receiver electrodes.

Figure 10:
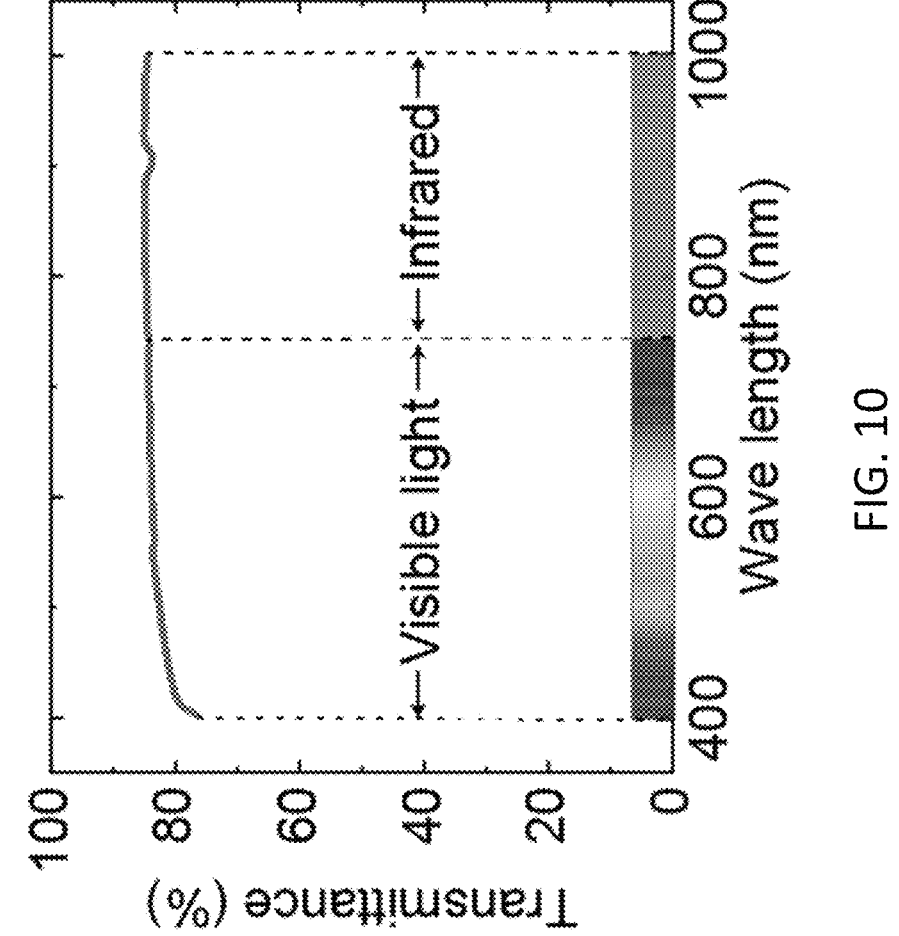
FIG. 10 shows light transmission of an electronic skin provided by the present invention.

In some embodiments, the control circuit is formed on the patterned transparent and flexible substrate by: transfer printing a conductive trace pattern from a donor substrate to the patterned transparent and flexible substrate; and attaching electronic components on the patterned transparent and flexible substrate to form the control circuit.
Performance Evaluation FIG. 10 shows light transmission of an electronic skin provided by the present invention. As shown, the electronic skin demonstrates a light transmission of more than 80% in the 410 nm-1000 nm range. Such high level of transparency allows the electronic skin to be used as a transparent 3D sensing and gesture recognition layer. For example, the electronic skin can be directly applied on a display or an infrared sensor, without blocking any line of sight. Furthermore, the transparency of the electronic skin allows for its integration, as a virtually invisible surface layer, into existing devices without changing the aesthetic of the device.

Figures 11, 12:
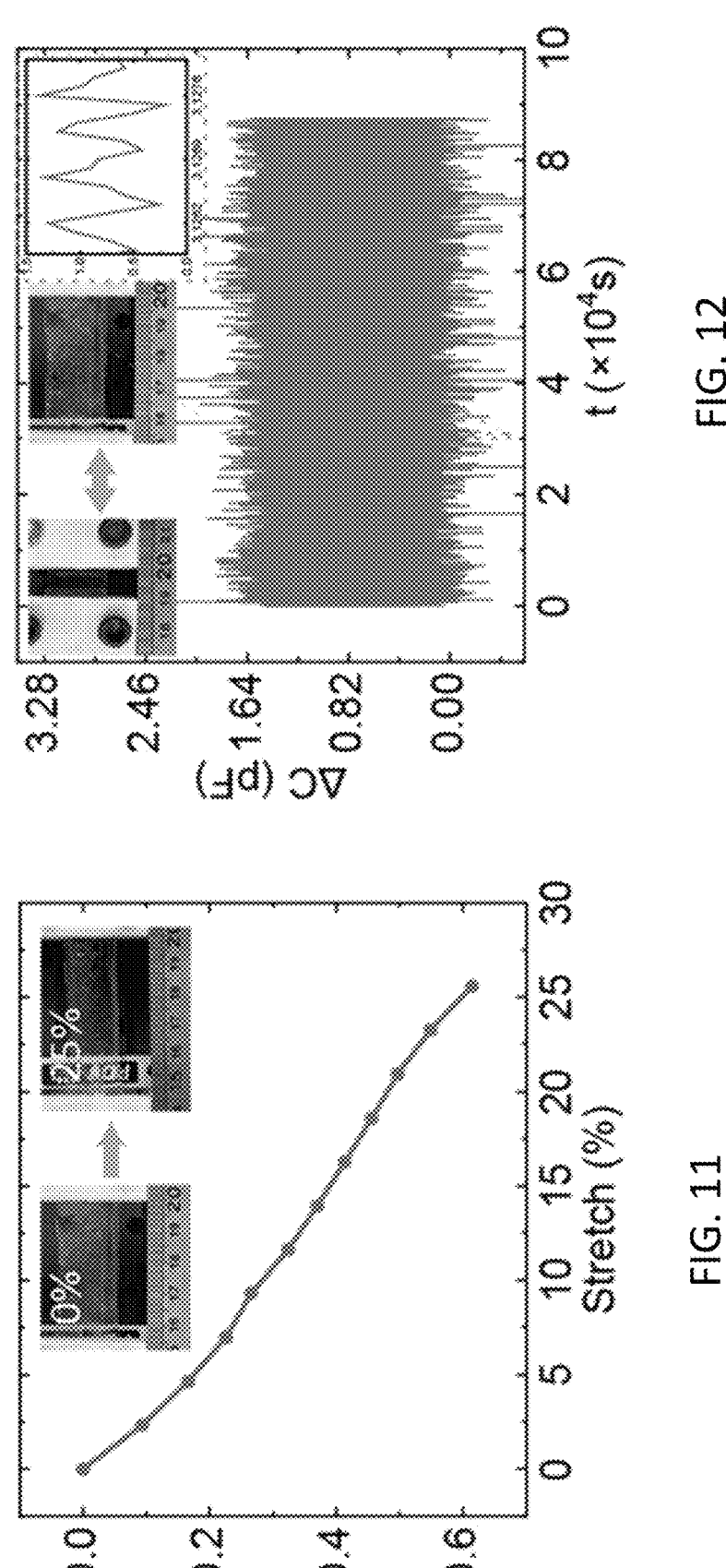
FIG. 11 shows the change in capacitance during the stretching of the electronic skin for 25% from its original length.
FIG. 12 performance of the electronic skin after more than 8000 cycles of folds and unfolds.

FIG. 11 shows the change in capacitance during the stretching of an electronic skin provided by the present invention from its original length to 25%. FIG. 12 shows that there was no significant change in device performance after more than 8000 folds and unfolds. Because conductive biogel is used to make the electrodes, there is no fatigue effect like that of metals which can experience wear and tear over time. This means that the electronic skin can be stretched and bent repeatedly without experiencing any damage.

Figure 13:
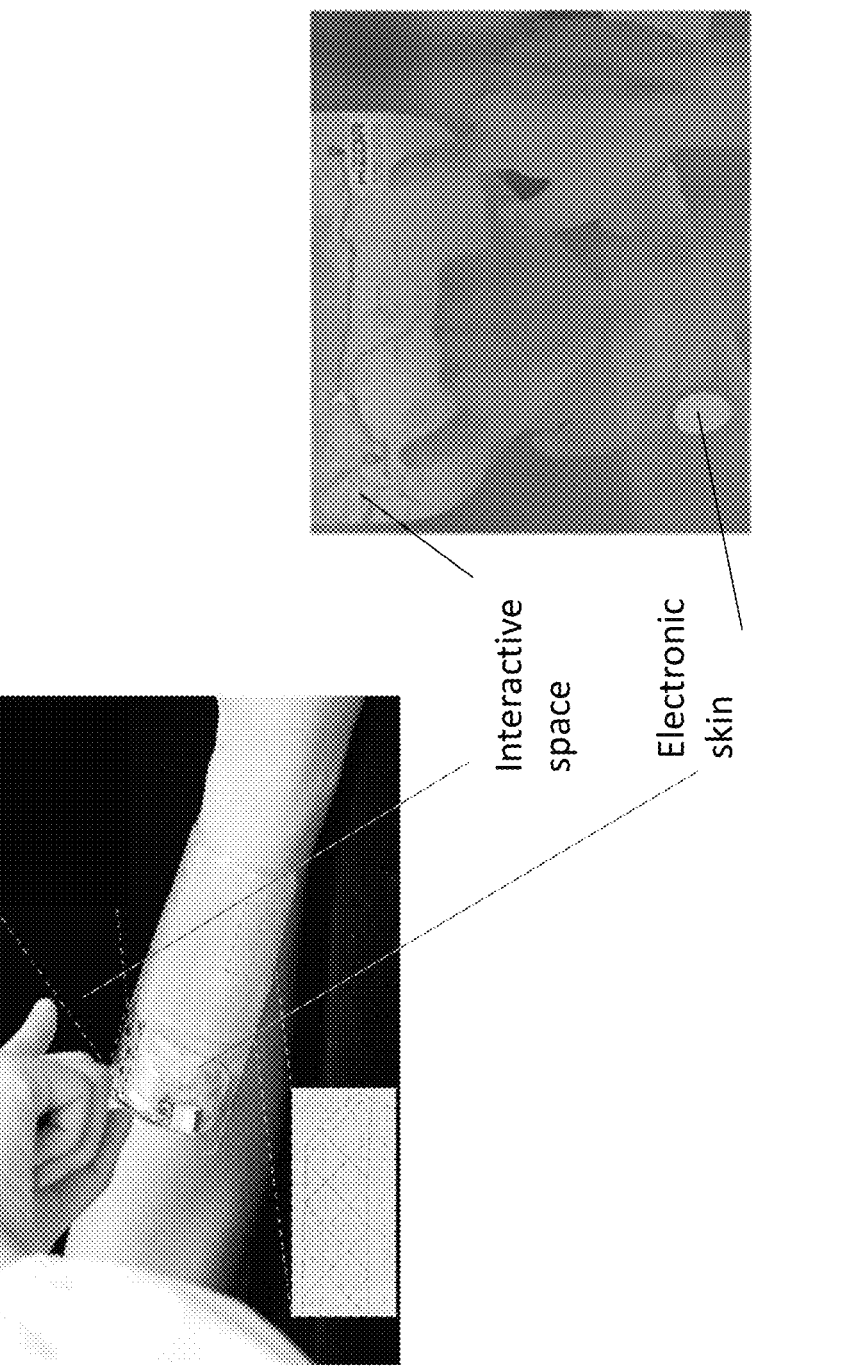
FIG. 13 shows how the electronic skin is used to collect and process sensing signals due to proximity of a user's finger to obtain three-dimensional space coordinates of the finger within a predefined interactive space.
Figure 14:
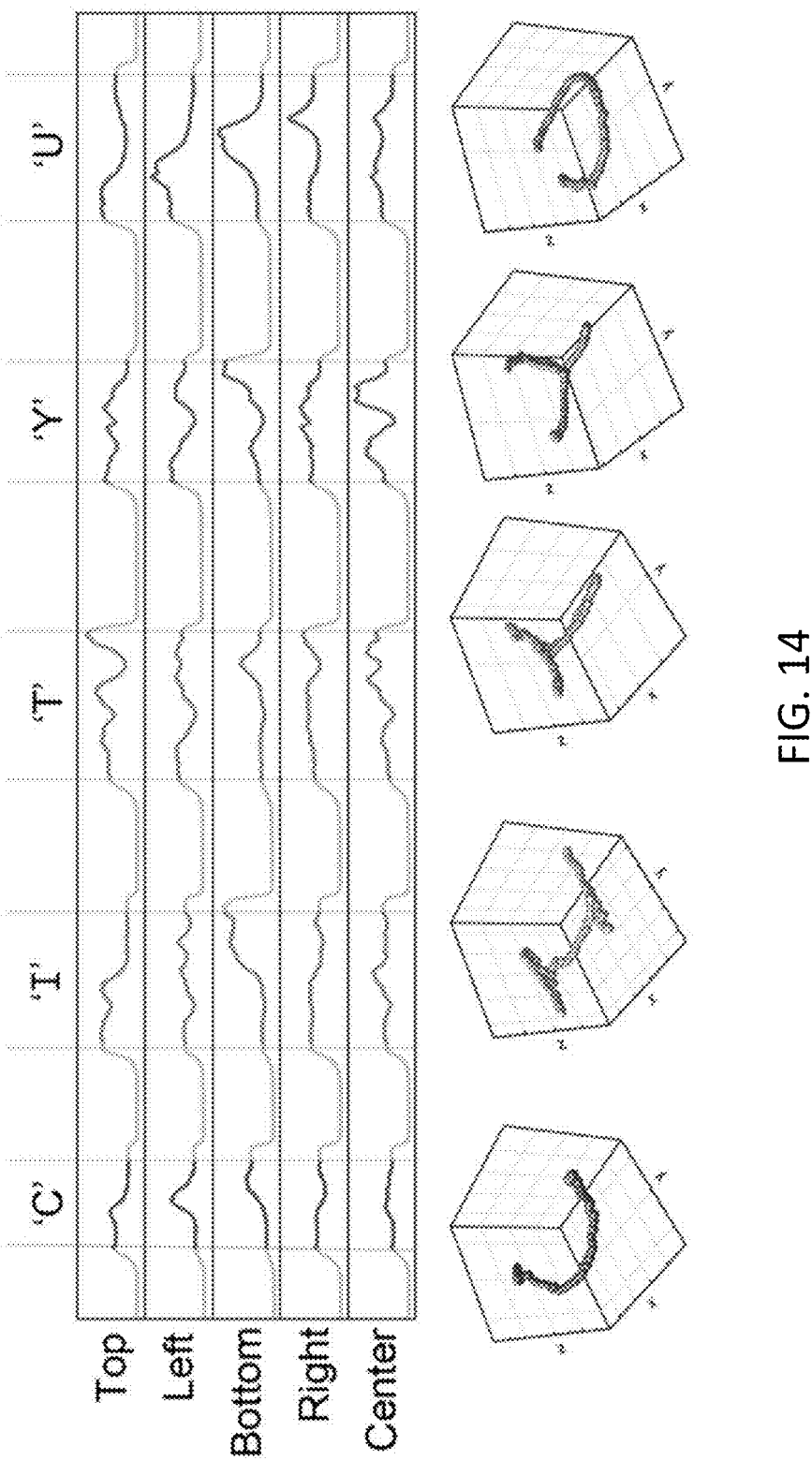
FIG. 14 shows the sensing signals received by the electronic skin and the finger movement trajectory calculated when using the finger to write five letters "CITYU" in the predefined interactive space.

The electronic skin provided by the present invention can be used for gesture recognition and finger position tracking. As shown in FIG. 13, the electronic skin may be used to collect and process sensing signals due to proximity of a user's finger to obtain three-dimensional space coordinates of the finger within a predefined interactive space. FIG. 14 shows the sensing signals received by the electronic skin and the finger movement trajectory calculated when using a finger to write five letters "CITYU" in the predefined interactive space. The electronic skin is very suitable for 3D modeling, AR/VR, wearable devices and other applications that need to operate in three-dimensional space.

For instance, the electronic skin can also be used to empower a robot or a drone to perceive its surroundings more effectively and provide a more comprehensive solution for 3D object detection and distance measurement. For instance, a robot arm can use the electronic skin to judge the distance between a target or whether it has grasped the target. A drone can use the electronic skin to determine whether there are obstacles such as an electric cable on its path.

In underwater applications, the electronic skin can serve as a gesture recognition sensor in murky water to help divers to communicate effectively when their sight is blocked. This technology can also be used to monitor sea life and study collective animal behavior in the wild. This technology can help us to understand and protect marine ecosystems and the species that inhabit them.

The foregoing description of the present invention has been provided for the purposes of illustration and description. It is not intended to be exhaustive or to limit the invention to the precise forms disclosed. Many modifications and variations will be apparent to the practitioner skilled in the art.

The embodiments were chosen and described in order to best explain the principles of the invention and its practical application, thereby enabling others skilled in the art to understand the invention for various embodiments and with various modifications that are suited to the particular use contemplated.

What is claimed is:

1. A transparent and flexible electronic skin with three-dimensional sensing capability, comprising:
   a transparent and flexible substrate;
   a transparent and flexible electric field sensor disposed on the substrate and comprising:
      a transparent and flexible transmitter electrode;
      one or more transparent and flexible receiver electrodes; and
      a transparent and flexible dielectric layer disposed between the transmitter electrode and the one or more receiver electrodes;
   a control circuit disposed on the substrate and connected to the electric field sensor; and
   a transparent and flexible protective layer encapsulating the electric field sensor and the control circuit; and
   wherein the control circuit is configured to:
      drive the transmitter electrode to transmit a reference signal to establish a quasi-static electrical near field around the electric field sensor; and
      process one or more measurement signals received by the one or more receiver electrodes respectively, each measurement signal is indicative of a distortion of the quasi-static electrical near field due to proximity of an object to a corresponding receiver electrode; and
   wherein the transparent and flexible transmitter and receiver electrodes are made of a conductive transparent gel.

2. The transparent and flexible electronic skin according to claim 1, wherein the one or more receiver electrodes include:
   a central receiver electrode positioned at a central region of the electric field sensor; and
   four peripheral receiver electrodes positioned at four peripheral regions of the electric filed sensor respectively.

3. The transparent and flexible electronic skin according to claim 1, wherein the transparent and flexible substrate are made of polydimethylsiloxane.

4. The transparent and flexible electronic skin according to claim 1, wherein the transparent and flexible protective layer are made of polydimethylsiloxane.

5. The transparent and flexible electronic skin according to claim 1, wherein the transparent and flexible dielectric layer is made of polydimethylsiloxane.

6. The transparent and flexible electronic skin according to claim 1, wherein the conductive transparent gel contains sodium ions.

7. The transparent and flexible electronic skin according to claim 1, wherein the control circuit comprises:

a signal driver configured to drive the transmitter electrode to transmit the reference signal; and an analogy-to-digital converter configured to convert the one or more measurement signals to one or more digital signals respectively.

8. The transparent and flexible electronic skin according to claim 7, wherein the control circuit further comprises a microprocessor configured to:

process the one or more digital signals to calculate one or more distances of the object relative to the one or more receiver electrodes respectively; and analyse the one or more calculated distances to determine a position/gesture data of the object.

9. The transparent and flexible electronic skin according to claim 8, the control circuit further comprises a wireless communication unit configured to send the position/gesture data to a remote device.

10. The transparent and flexible electronic skin according to claim 9, wherein the distance of the object relative to each of the one or more receiver electrode is calculated by the processor based on a least squares multilateration algorithm.

11. The transparent and flexible electronic skin according to claim 1, further comprising a lithium-ion battery for supplying power to the control unit; and a wireless charging unit configured to receive electromagnetic energy and convert the received electromagnetic energy into DC voltage to charge the lithium-ion battery.

12. A method for fabricating a transparent and flexible electronic skin, comprising:

moulding a transparent and flexible material to form a patterned transparent and flexible substrate;

dispensing a first conductive transparent gel on the patterned transparent and flexible substrate to form a transmitter electrode;

forming a control circuit on the patterned transparent and flexible substrate;

moulding the transparent and flexible material to form a patterned transparent and flexible dielectric layer;

dispensing a second conductive transparent gel on the patterned transparent and flexible dielectric layer to form one or more receiver electrodes;

attaching the dielectric layer on the substrate such that the transmitter electrode is spaced apart from the one or more receiver electrodes through the dielectric layer to form an electric filed sensor; and encapsulating the control circuit and the electric field sensor with the transparent and flexible material.

13. The method according to claim 12, wherein the control circuit is formed on the patterned transparent and flexible substrate by:

transfer printing a conductive trace pattern from a donor substrate to the patterned transparent and flexible substrate; and attaching electronic components on the patterned transparent and flexible substrate to form the control circuit.

14. The method according to claim 12, wherein each of the first and second the conductive transparent gels is prepared by:

dissolving sodium chloride, citric acid, sodium citrate and glycerol in deionized water to form a first solution; and dissolving gelatin powder in the first solution to form the conductive transparent gel.

\* \* \* \* \*